US008721538B2

(12) United States Patent
Bucholz

(10) Patent No.: US 8,721,538 B2
(45) Date of Patent: May 13, 2014

(54) DISTRACTOR

(75) Inventor: Richard D. Bucholz, Ladue, MO (US)

(73) Assignee: St. Louis University, St. Louis, MO (US)

( * ) Notice: Subject to any disclaimer, the term of this patent is extended or adjusted under 35 U.S.C. 154(b) by 0 days.

(21) Appl. No.: 13/014,473

(22) Filed: Jan. 26, 2011

(65) Prior Publication Data

US 2011/0275902 A1 Nov. 10, 2011

Related U.S. Application Data

(60) Provisional application No. 61/333,042, filed on May 10, 2010, provisional application No. 61/349,331, filed on May 28, 2010.

(51) Int. Cl.
*A61B 17/02* (2006.01)
(52) U.S. Cl.
USPC .......................................... 600/208; 600/206
(58) Field of Classification Search
USPC .................................................. 600/201–246
See application file for complete search history.

(56) References Cited

U.S. PATENT DOCUMENTS

| | | | | |
|---|---|---|---|---|
| 2,313,164 A * | 3/1943 | Nelson | ........................... | 600/208 |
| 3,030,947 A * | 4/1962 | Engelbert | ..................... | 600/213 |
| 4,411,655 A | 10/1983 | Schreck | | |
| 4,921,479 A * | 5/1990 | Grayzel | ........................ | 604/509 |
| 4,945,896 A | 8/1990 | Gade | | |
| 5,133,720 A | 7/1992 | Greenberg | | |
| 5,139,511 A * | 8/1992 | Gill et al. | ...................... | 606/198 |
| 5,147,370 A | 9/1992 | McNamara et al. | | |
| 5,284,129 A | 2/1994 | Agbodoe et al. | | |
| 5,616,131 A | 4/1997 | Sauer et al. | | |
| 6,007,487 A | 12/1999 | Foley et al. | | |
| 6,106,642 A | 8/2000 | DiCarlo et al. | | |
| 6,120,535 A * | 9/2000 | McDonald et al. | .......... | 623/1.39 |
| 6,273,853 B1 | 8/2001 | Cartier et al. | | |
| 6,364,833 B1 | 4/2002 | Valerio et al. | | |
| 6,425,859 B1 | 7/2002 | Foley et al. | | |
| 6,475,142 B1 | 11/2002 | Parsons et al. | | |
| 6,599,240 B2 | 7/2003 | Puchovsky et al. | | |
| 6,916,287 B2 * | 7/2005 | Dematteis et al. | ............ | 600/184 |
| 6,932,764 B2 * | 8/2005 | Kashyap | ....................... | 600/210 |
| 7,052,454 B2 * | 5/2006 | Taylor | ............................ | 600/114 |
| 7,276,047 B2 | 10/2007 | Sakal et al. | | |
| 7,699,864 B2 * | 4/2010 | Kick et al. | ..................... | 606/198 |
| 2001/0034473 A1 | 10/2001 | Cartier et al. | | |
| 2002/0077531 A1 | 6/2002 | Puchovsky et al. | | |
| 2003/0069476 A1 * | 4/2003 | Deslauriers et al. | .......... | 600/207 |
| 2003/0073998 A1 * | 4/2003 | Pagliuca et al. | ................. | 606/61 |
| 2003/0097045 A1 | 5/2003 | Kashyap | | |

(Continued)

*Primary Examiner* — Jerry Cumberledge
(74) *Attorney, Agent, or Firm* — Senniger Powers LLP

(57) ABSTRACT

A surgical distractor for distracting tissue of a patient to access structure underlying the tissue of the patient. The distractor includes a tube having a distal end adapted for insertion in tissue, a proximal end opposite the distal end, an exterior surface adapted for contacting the tissue, and an interior surface opposite the exterior surface defining a hollow interior extending between the distal end and the proximal end for accessing structure underlying the tissue when the distal end is inserted in the tissue. The distractor is adjustable from a reduced configuration, in which the tube has a reduced width sized for inserting the distal end in the tissue, and an expanded configuration, in which the tube has an expanded width greater than the reduced width sized to provide the hollow interior with a size sufficient for accessing the structure underlying the tissue.

18 Claims, 8 Drawing Sheets

(56) References Cited

U.S. PATENT DOCUMENTS

| | | | |
|---|---|---|---|
| 2005/0075540 A1* | 4/2005 | Shluzas et al. | 600/203 |
| 2005/0222576 A1* | 10/2005 | Kick et al. | 606/104 |
| 2005/0273132 A1* | 12/2005 | Shluzas et al. | 606/198 |
| 2006/0089536 A1* | 4/2006 | Perez-Cruet et al. | 600/210 |
| 2007/0032703 A1* | 2/2007 | Sankaran et al. | 600/208 |
| 2007/0038032 A1* | 2/2007 | De Canniere et al. | 600/210 |
| 2007/0270898 A1 | 11/2007 | Lillehei | |
| 2008/0058604 A1* | 3/2008 | Sorensen | 600/208 |
| 2008/0058605 A1* | 3/2008 | Sorensen | 600/208 |
| 2008/0183044 A1 | 7/2008 | Colleran et al. | |
| 2008/0221394 A1 | 9/2008 | Melkent et al. | |
| 2008/0319268 A1 | 12/2008 | Michaeli et al. | |

\* cited by examiner

DISTRACTOR

CROSS REFERENCE TO RELATED APPLICATION

This Application claims priority under 35 U.S.C. §119(e) from U.S. Provisional Patent Applications 61/333,042 filed on May 10, 2010, and 61/349,331 filed on May 28, 2010, which are hereby incorporated by reference in its entirety.

FIELD OF THE INVENTION

The present invention relates to a surgical distractor, and more particularly to a distractor for distracting brain tissue.

BACKGROUND

Lesions and other anomalies in the brain can be treated or removed by entering the brain through the cerebral cortex (i.e., the outer layer of the brain) to access the underlying anomaly or other target. When entering through the cortex, tears and other damage can occur, resulting in neurological deficit, because the cortex is responsible for higher brain functions, including sensation, voluntary muscle control, thought, reasoning, and memory. Thus, the cortex tissue is preferably distracted rather than cut or torn. However, the gelatinous nature of the brain results in the cortex tissue returning to its original shape, blocking the surgeon's access to the target. In the past, surgeons frequently cut and removed the obscuring tissue, leading to cortex damage. Thus, there is a need for a distractor that displaces brain tissue without damaging the tissue and preventing the tissue from returning to its original location during surgery.

SUMMARY

The present invention relates to a surgical distractor for distracting tissue of a patient to access structure underlying the tissue of the patient. The distractor includes a tube having a distal end adapted for insertion in tissue, a proximal end opposite the distal end, an exterior surface adapted for contacting the tissue, and an interior surface opposite the exterior surface defining a hollow interior extending between the distal end and the proximal end for accessing structure underlying the tissue when the distal end is inserted in the tissue. The distractor is adjustable from a reduced configuration, in which the tube has a reduced width sized for inserting the distal end in the tissue, and an expanded configuration, in which the tube has an expanded width greater than the reduced width sized to provide the hollow interior with a size sufficient for accessing the structure underlying the tissue.

In another aspect, the present invention relates to a surgical distractor for distracting tissue of a patient to access structure underlying the tissue of the patient. The distractor includes a sheet formed to have a spiral cross section, the sheet having an exterior surface adapted for contacting the tissue, and an interior surface opposite the exterior surface, defining a tubular hollow interior, the spiral cross section being adjustable from a reduced configuration, in which the cross section has a reduced width sized for insertion in the tissue, and an expanded configuration, in which the cross section has an expanded width greater than the reduced width and the hollow interior has a width sized to provide access to the structure underlying the tissue through the hollow interior.

In yet another aspect, the present invention includes a surgical distractor for distracting tissue of a patient to access structure underlying the tissue of the patient. The distractor includes a conduit. The distractor also includes a sheet connected to the conduit and wound around the conduit so the sheet has a spiral cross section, the sheet having an exterior surface adapted for contacting the tissue, and an interior surface opposite the exterior surface, defining a tubular hollow interior, the spiral cross section being adjustable from a reduced configuration, in which the cross section has a reduced width sized for insertion in the tissue, and an expanded configuration, in which the cross section has an expanded width greater than the reduced width and the hollow interior has a width sized to provide access to the structure underlying the tissue through the hollow interior.

In a further aspect, the present invention includes a method of distracting tissue of a patient to access structure underlying the tissue of the patient. The method includes introducing a distal end of a tube into tissue of the patient. The tube is made of a material having shape memory and a transition temperature that is lower than an anticipated body temperature of the patient. The method also includes adjusting a band surrounding the tube for limiting an expanded width of the tube. The method also includes allowing the tube to expand due to increasing temperature caused by the tube being introduced into the tissue of the patient. The method also includes accessing structure underlying the tissue of the patient through a hollow interior of the expanded tube.

BRIEF DESCRIPTION OF THE DRAWINGS

Corresponding reference characters indicate corresponding parts throughout the drawings.

DETAILED DESCRIPTION OF THE DRAWINGS

Figure 1:
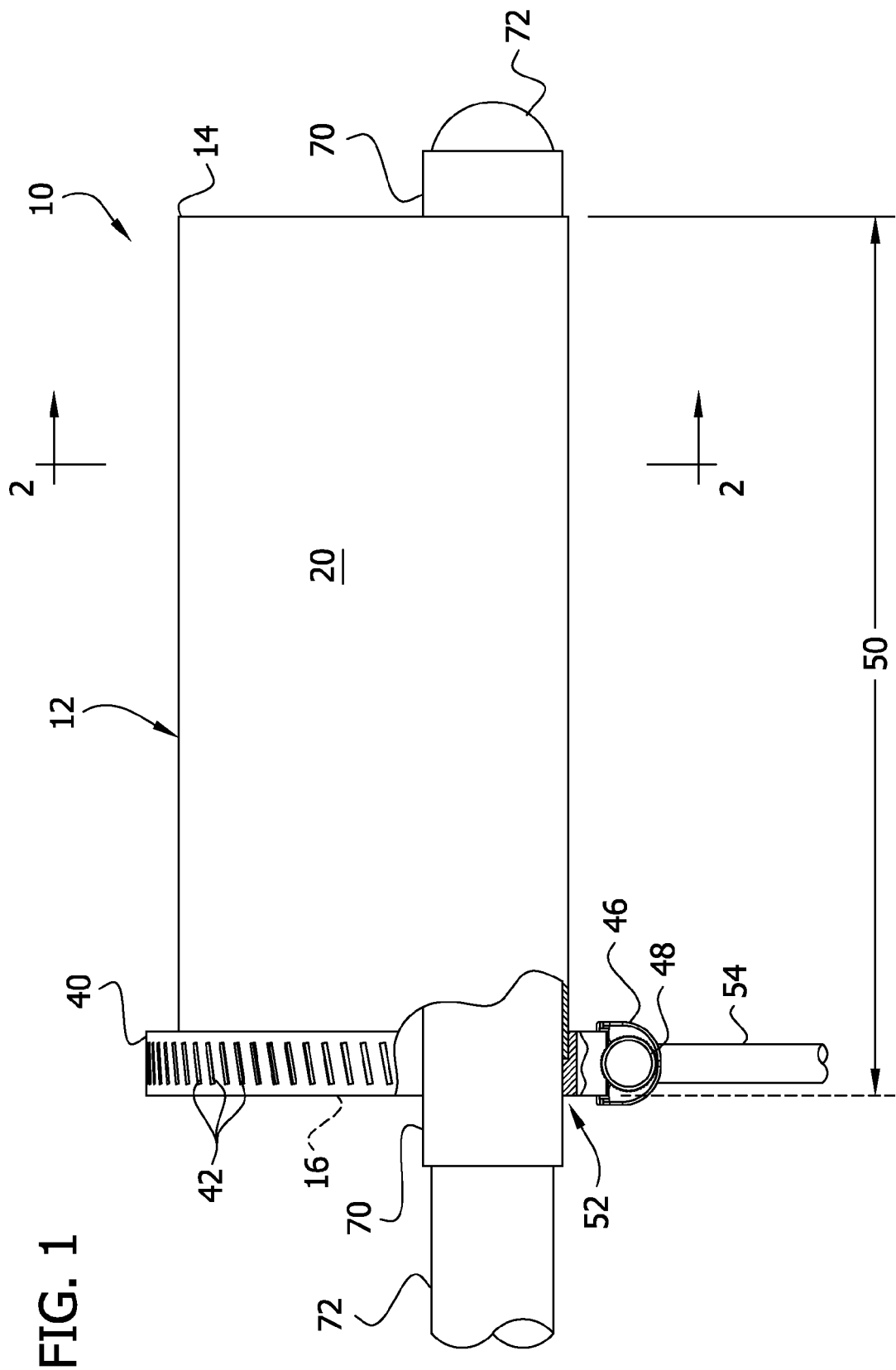
FIG. 1 is a side elevation of a surgical distractor of a first embodiment of the present invention.
Figure 3A:
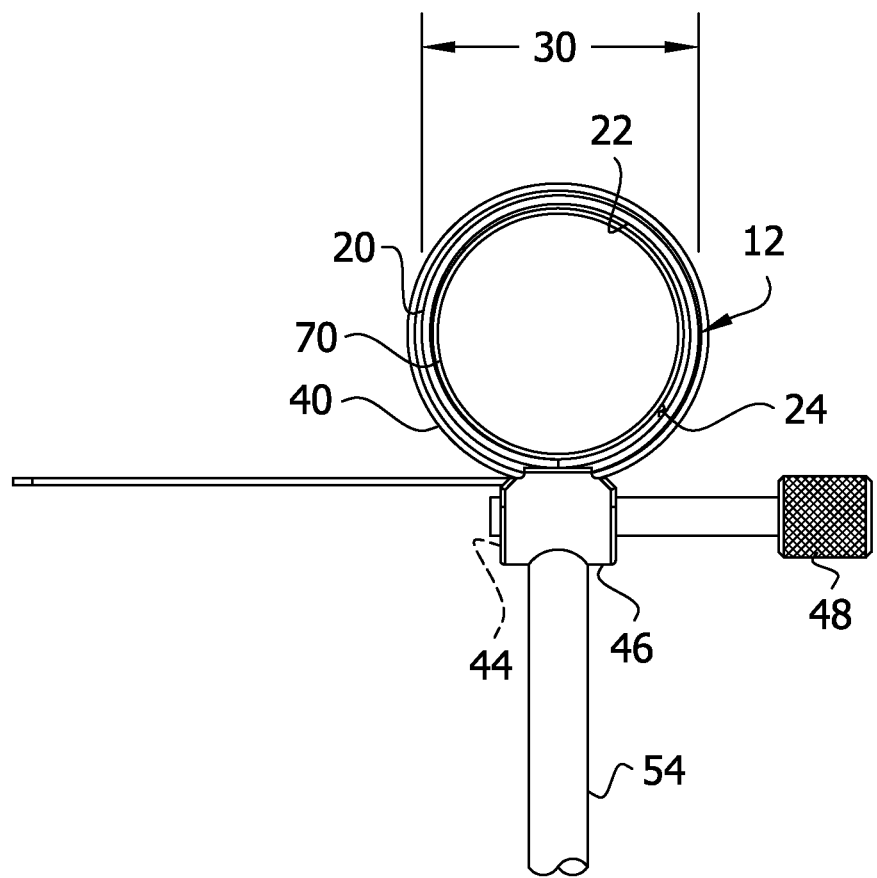
FIG. 3A is an end elevation of the distractor of FIG. 1 in a reduced configuration.
Figure 4:
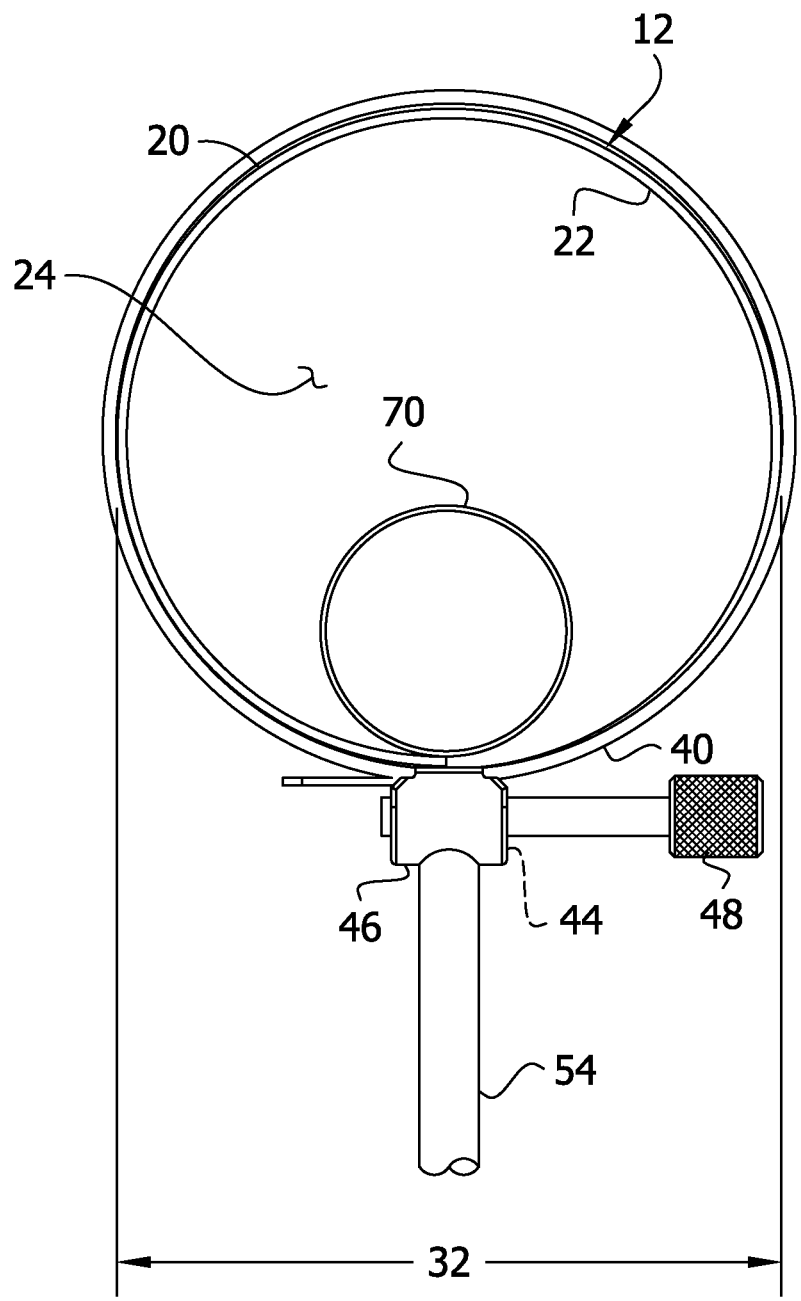
FIG. 4 is an end elevation of the distractor of FIG. 1 in an expanded configuration.

Referring to FIG. 1, a surgical distractor for distracting tissue such as cortex tissue to access structure underlying the tissue is generally indicated by the reference number 10. The distractor 10 includes a tube, generally designated by 12, formed from a sheet wound into a spiral. The tube 12 has a distal end 14, which is shaped to be inserted in the tissue with minimal damage to the tissue. For example, the edges of the distal end 14 may be rounded to prevent them from cutting tissue as they enter it. The tube 12 also includes a proximal end 16 opposite the distal end 14. An external surface 20 of the tube 12 faces the tissue to contact the tissue in use. An interior surface 22 (FIG. 2) opposite the external surface 20 defines a hollow interior 24 of the tube 12 extending between the distal end 14 and the proximal end 16. A surgeon accesses structure underlying the tissue distracted by the distractor 10 by entering through the hollow interior 24. As will be explained in further detail below, the distractor 10 is adjustable from a reduced configuration as shown in FIG. 3A, in which the tube 12 has a reduced width 30 sized for inserting the distal end 14 into the tissue, and an expanded configuration as shown in FIG. 4, in which the tube 12 has an expanded width 32 greater than the reduced width. The expanded width 32 provides the hollow interior 24 with a size sufficient for accessing the structure underlying the tissue.

The tube 12 is made of a material such as nitinol having shape memory. Such materials are able to be deformed at one temperature and recover to their original, undeformed shape when heated above a transition temperature. Preferably, the material used in making the tube 12 has a transition temperature lower than an anticipated body temperature of the patient. Because such materials are well known and readily available to those skilled in the art, they will not be described in further detail.

As further illustrated in FIG. 1, a restraint device such as a band 40 surrounds the tube 12 for limiting the expanded width 32 of the tube. In some embodiments, the band 40 has an adjustable circumference for changing the expanded width 32. For example, in one embodiment, the band 40 includes a series of laterally extending slots 42 formed in the band adjacent one circumferential end. An opposite end of the band 40 includes an opening 44 sized and shaped for receiving the first end of the band. A housing 46 adjacent the opening 44 receives a worm screw 48 that engages the slots 42 in the band 40. As will be apparent to those skilled in the art, the slots 42 in the band 40 form a rack. The worm screw 48 may be rotated in the housing 44 to adjust the circumference of the band 40.

Figure 7:
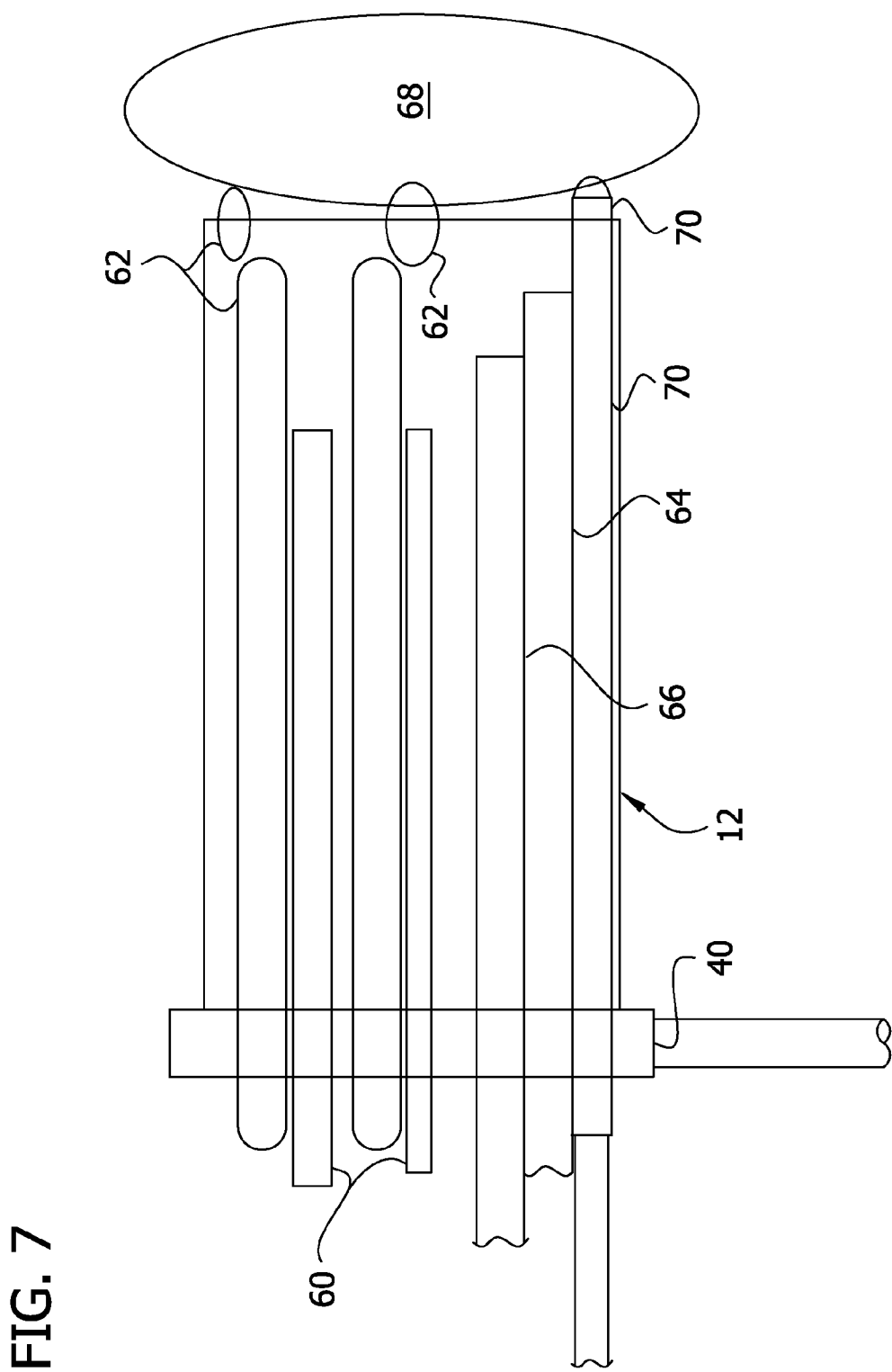
FIG. 7 is a schematic side elevation of the distractor having instruments.

Although the tube may have other dimensions without departing the scope of the present invention, in one embodiment the tube has a length 50 in a range of about 1.5 cm to about 3.0 cm. The band 40 may include a ledge 52 for receiving the tube 12. In one embodiment, a short sector of the tube 12 is brazed to the ledge 52 of the band 40 to fasten the components together. In some embodiments, the band 40 includes a handle 54 for holding and manipulating the distractor 10 into position. The tube 12 has a reduced width 30 in a range of about 2.5 mm to about 3.0 mm, and an expanded width in a range of about 1.8 cm to about 2.0 cm. Thus, in the expanded configuration, the tube 12 has an expanded width 32 greater than the reduced width 30. Further, the expanded width is large enough to provide the hollow interior 24 with a size sufficient for receiving instruments to repair, remove, perform surgical procedures on, illuminate, suction, irrigate, visualize, or otherwise access the underlying tissue without damaging the distracted tissue as shown in FIG. 7. Such instruments may include robotic equipment such as robots 60 having end effectors 62, endoscopic equipment such as endoscopes 64, and fluid handling equipments such as irrigation conduits 66 that are used to treat tissue in a target area 68.

Figure 2:
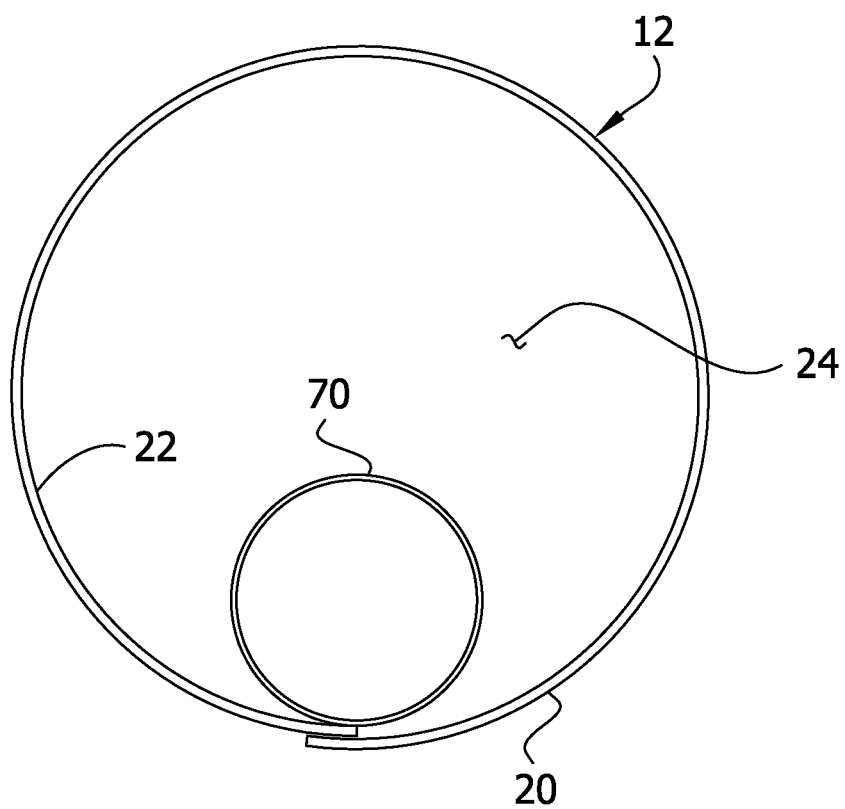
FIG. 2 is a cross section of the distractor taken in the plane of line 2-2 of FIG. 1.

As shown in FIGS. 2-4, the tube 12 in one embodiment has a generally cylindrical shape in the expanded configuration. Further, the spiral cross section has at least one complete turn in the expanded configuration so the tissue surrounding the exterior surface 20 of the distractor 10 is in substantially uninterrupted contact with the exterior surface to prevent it from returning to its reduced configuration. This configuration also minimizes stress in the distracted tissue to limit damage.

In some embodiments, the distractor may include a conduit 70 extending through the hollow interior 24 of the tube 12 from the distal end 14 to the proximal end 16. In one embodiment, the sheet used to form the tube 12 is connected to the conduit 70 and wound around the conduit to form the tubular hollow interior 24. The conduit may be used to apply suction to the target area to clear fluids. Although the band 40 and conduit 70 may be made of other materials without departing from the scope of the present invention, in one embodiment, these elements are made of stainless steel. Although the conduit 70 may be attached to the sheet in other ways without departing from the scope of the present invention, in one embodiment, the conduit is brazed to the sheet. It is envisioned that an obturator 72 having a rounded end may be inserted into the conduit 70 when the tube 12 is inserted into the brain to prevent the end of the conduit from damaging the brain. Once the distractor 10 is in position, the obturator 12 may be removed, allowing the conduit 70 to be used to draw fluid from the target area 68.

Figure 3B:
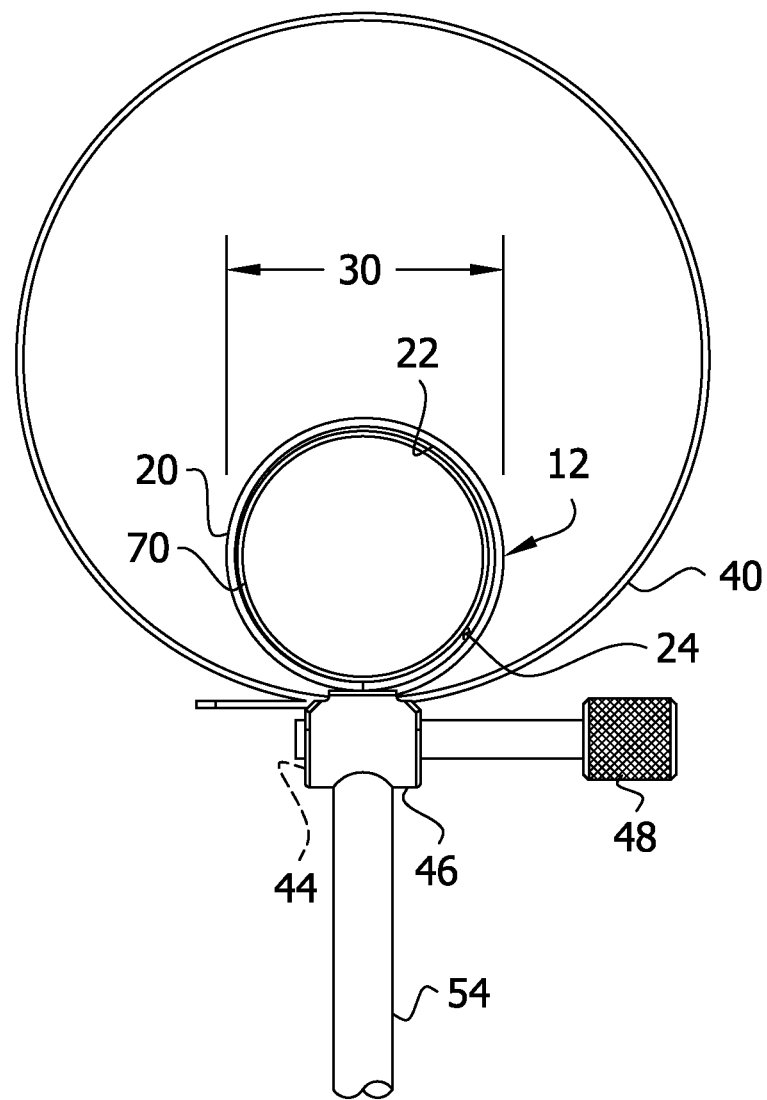
FIG. 3B is an end elevation of the distractor of FIG. 1 in a reduced configuration showing a restraint device expanded.

To use the distractor 10 described above to distract tissue of a patient to access structure underlying the tissue, a surgeon introduces the distal end 14 of the tube 12 into tissue of the patient. As shown in FIG. 3A, the band 40 is initially adjusted to limit a reduced width 30 of the tube 12. After insertion into tissue of the patent, the band 40 is adjusted to limit an expanded width 32 of the tube 12 as shown in FIG. 3B. The surgeon allows the tube 12 to expand under the influence of increased temperature caused by the tube being introduced into the tissue of the patient. Once expanded as illustrated in FIG. 4, the surgeon accesses the structure underlying the tissue of the patient through the hollow interior 24 of the expanded tube 12. After access is no longer needed, the surgeon cools the tube 12 to a temperature below the transition temperature and removes the tube from the tissue of the patient.

In one embodiment, the distractor 10 of the present invention may be used by generating a surgical plan with a navigational device (e.g., robotic actuators) allowing access to a deep seated anomaly (e.g., a lesion) in a brain, preferably avoiding major fiber tracts and key areas of the cortex. The surgical path could be followed by holding the distractor 10 with a gripping instrument (not shown) that holds the handle 54 and/or proximal end 16 of the distractor or by a robotic positioning device (not shown) that would precisely align the distractor with the surgical path and insert the distractor while in the reduced configuration to the level of the deep target 68. Once in position, the band 40 would be opened to the desired diameter. The heat of the brain would cause the metal to return to its expanded configuration. The tube 12 would expand, placing uniform pressure on the brain symmetrically in all directions and minimizing damage to the cortex.

Once the distractor 10 is expanded, the conduit 70 would be at the base of the surgical path to the target 68. In this position, the obturator 72 could be removed from the conduit 70 permitting fluid to be drawn from the target and into suction tubing (not shown) attached to the conduit. Other instruments could provide illumination and visualization (e.g., endoscope 64). In this way, unobstructed, illuminated, and stable access to the target is provided. Further, micro-instruments could be used to remove the anomaly (e.g., lesion). For example, robotic devices 60 capable of guidance and movement on a microscopic level could be inserted through the surgical channel (i.e., the hollow interior 24) while their control and power sources (not shown) could remain outside the brain. Because the control and power systems to the robotic devices are outside the brain and illumination and visualization occurs toward the distal end 14 of the distractor 10, the control and power sources would be in a position where they would not block illumination and visualization, even when multiple robotic devices are used.

The diameter of the final opening could be less than the diameter of the target 68 if resection is carried out by devices that have degrees of freedom within the body part undergoing surgery. By flexing deep within the surgical path, resection of tissue could be carried out beyond an area of direct visualization through the end of the distractor 10. Optional force detectors could be embedded in the side of the distractor 20 to determine an amount of force being exerted on the sides of the distractor. Through the use of animal studies, with different degrees of force being exerted against the brain, those skilled in the art could determine how much force can be exerted without causing tearing of fiber tracts and vessels. Thereafter, the force detectors could measure forces exerted by the distractor as it is opened to warn a user when too much force is being applied to the brain.

At the conclusion of the procedure, the surgical channel could be irrigated with cold fluid such as saline, causing the metal to once again reduce in diameter at least slightly. This would move the distractor away from the surrounding brain tissue and allow extraction without causing additional injury to the brain.

Figure 5:
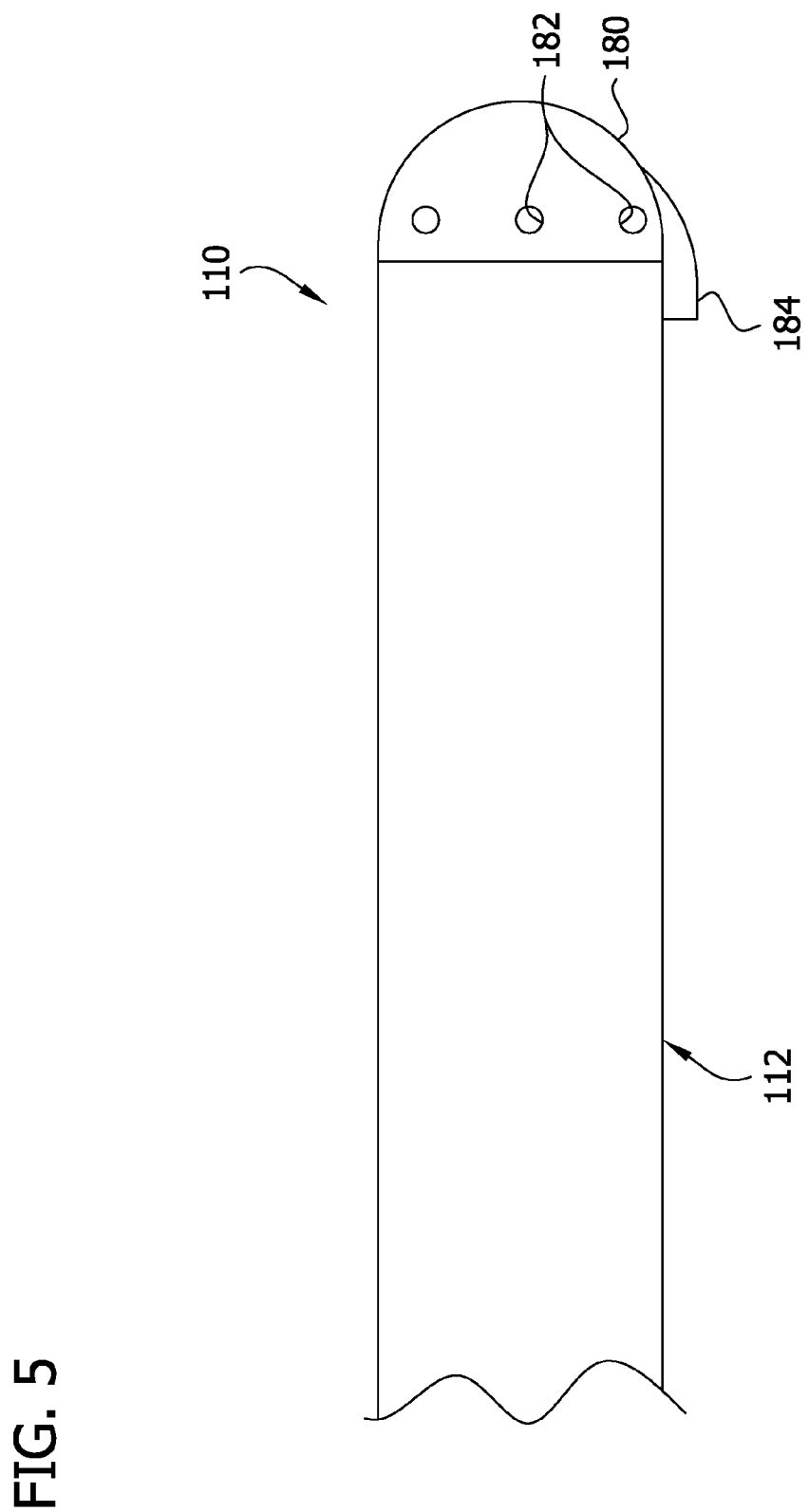
FIG. 5 is a side elevation of a surgical distractor of a second embodiment of the present invention in a reduced configuration.
Figure 6:
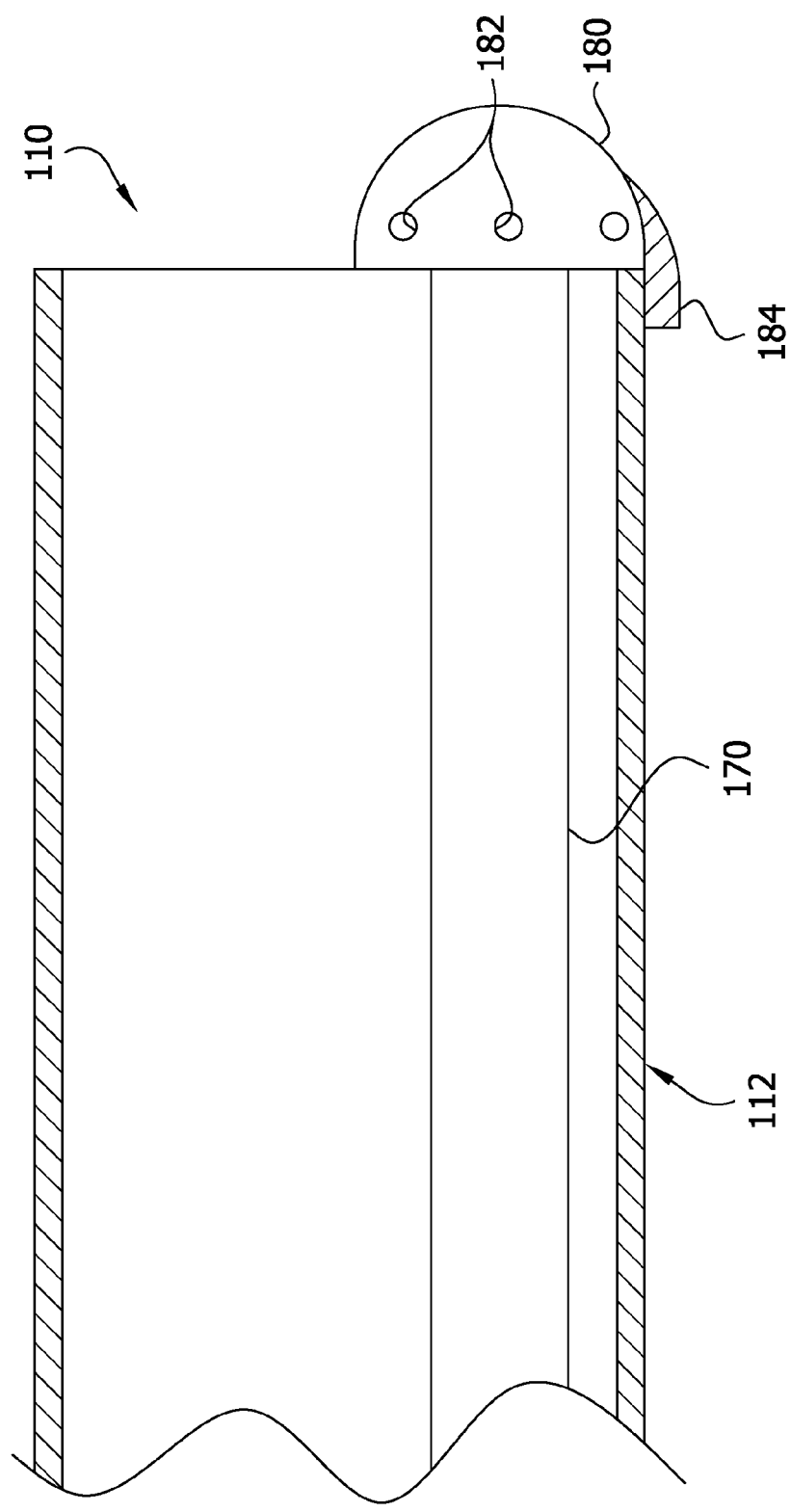
FIG. 6 is a vertical cross section of the distractor of the second embodiment in the expanded configuration.

As illustrated in FIGS. 5 and 6, a second embodiment of a surgical distractor of the present invention is generally indicated by the reference number 110. The distractor 110 includes a tube, generally designated by 112, similar to the tube 12 of the first embodiment. Accordingly, the tube 112 expands from a reduced configuration as shown in FIG. 5. to an expanded configuration as shown in FIG. 6 when it reaches a transition temperature. The distractor 110 also includes a conduit 170 *FIG. 6) extending through the tube 112. Rather than having an open distal end as in the first embodiment, the conduit 170 of the second embodiment includes a rounded end cap 180 to prevent damage to tissue as the distractor 110 is inserted, thereby eliminating the need for an obturator. The rounded end cap 180 is ringed with openings 182 to permit liquid to enter the conduit 170 and be drawn away from the target as in the first embodiment. A tab 184 extends from the end cap 180 for attaching the tube 112 to the conduit 170. As will appreciated by those skilled in the art, attaching the tube 112 to the end cap 180 permits the distractor 110 of the second embodiment to operate in much the same way as the distractor 10 of the first embodiment. As other features of the distractors are similar, they will not be described in further detail.

In summary, the invention in one form comprises a heat sensitive distractor (not necessarily for use limited to the brain) that would dilate to develop a surgical approach path to a deep seated target. This distraction system allows the use of miniature robots deep in the body with "endo-wrists" (i.e. surgical arms with degrees of freedom towards their working end) that would allow the treatment (e.g., stimulation, drug implant, virus implant, etc.) or removal of target tissue deep within the body while producing minimal damage to adjacent and overlying tissue.

Having described the invention in detail, it will be apparent that modifications and variations are possible without departing from the scope of the invention defined in the appended claims.

When introducing elements of the present invention or the preferred embodiment(s) thereof, the articles "a", "an", "the", and "said" are intended to mean that there are one or more of the elements. The terms "comprising", "including", and "having" are intended to be inclusive and mean that there may be additional elements other than the listed elements.

As various changes could be made in the above constructions, products, and methods without departing from the scope of the invention, it is intended that all matter contained in the above description and shown in the accompanying drawings shall be interpreted as illustrative and not in a limiting sense.

What is claimed is:

1. A surgical distractor for distracting tissue of a patient to access structure underlying the tissue of the patient, said distractor comprising:
    a tube having a distal end adapted for insertion in tissue, a proximal end opposite the distal end, an exterior surface adapted for contacting the tissue, and an interior surface opposite said exterior surface defining a hollow interior extending between the distal end and the proximal end for accessing structure underlying the tissue when the distal end is inserted in the tissue, said distractor being adjustable from a reduced configuration, in which the tube has a reduced width sized for inserting the distal end in the tissue, and an expanded configuration, in which the tube has an expanded width greater than said reduced width sized to provide the hollow interior with a size sufficient for accessing the structure underlying the tissue, and
    a band having an inner surface surrounding said exterior surface of the tube for limiting the expanded width of the tube, the band including a rack and a worm screw for changing a peripheral length of the band so the band is adjustable for changing the expanded width.

2. A distractor as set forth in claim 1 wherein the tube comprises a sheet formed to have a spiral cross section.

3. A distractor as set forth in claim 2 wherein the sheet having the spiral cross section has at least one complete turn in the expanded configuration.

4. A distractor as set forth in claim 1 wherein the sheet is made of a material having shape memory.

5. A distractor as set forth in claim 4 wherein the material has a transition temperature lower than an anticipated body temperature of the patient.

6. A distractor as set forth in claim 1 further comprising a conduit positioned in the hollow interior of the tube for removing fluid from an area including the structure underlying the tissue of the patient.

7. A distractor as set forth in claim 1 wherein the tube has a length in a range of about 1.5 cm to about 3.0 cm.

8. A distractor as set forth in claim 1 wherein the tube has a reduced width in a range of about 2.5 mm to about 3.0 mm.

9. A distractor as set forth in claim 1 wherein the tube has an expanded width in a range of about 1.8 cm to about 2.0 cm.

10. A distractor as set forth in claim 1 wherein the tube has a generally cylindrical shape in the expanded configuration.

11. A distractor as set forth in claim 1 wherein the tube has an expanded width sized to provide the hollow interior with a size sufficient for holding an instrument selected from a group of instruments including robotic effectors and endoscopic equipment.

12. A surgical distractor for distracting tissue of a patient to access structure underlying the tissue of the patient, said distractor comprising a sheet formed to have a spiral cross section, the sheet having an exterior surface adapted for contacting the tissue, and an interior surface opposite said exterior surface, defining a tubular hollow interior, the spiral cross section being adjustable from a reduced configuration, in which the cross section has a reduced width sized for insertion in the tissue, and an expanded configuration, in which the cross section has an expanded width greater than said reduced width and the hollow interior has a width sized to provide access to the structure underlying the tissue through the hollow interior, said sheet being made from an alloy having shape memory so that the sheet remains in the reduced configuration when maintained below a transition temperature and seeks to recover to the expanded configuration when heated to a temperature above the transition temperature, the distractor further comprising a band surrounding the sheet for limiting the expanded width of the sheet, the band including a rack and a worm screw for changing a peripheral length of the band so the band is adjustable for changing the expanded width.

13. A distractor as set forth in claim 12 wherein the material has a transition temperature lower than an anticipated body temperature of the patient.

14. A distractor as set forth in claim 12 wherein the sheet having the spiral cross section has at least one complete turn in the expanded configuration.

15. A surgical distractor for distracting tissue of a patient to access structure underlying the tissue of the patient, said distractor comprising:
 a rigid conduit including a distal end having an opening and a proximal end opposite the distal end, said conduit being devoid of openings between the distal end and the proximal end;
 a sheet connected to the conduit and wound around the conduit so the sheet has a spiral cross section, the sheet having an exterior surface adapted for contacting the tissue, and an interior surface opposite said exterior surface, defining a tubular hollow interior, the spiral cross section being adjustable from a reduced configuration, in which the cross section has a reduced width sized for insertion in the tissue, and an expanded configuration, in which the cross section has an expanded width greater than said reduced width and the hollow interior has a width sized to provide access to the structure underlying the tissue through the hollow interior; and
 a band surrounding the sheet for limiting the expanded width of the sheet, the band including a rack and a worm screw for changing a peripheral length of the band so the band is adjustable for changing the expanded width.

16. A distractor as set forth in claim 15 wherein the sheet is made of a material having shape memory.

17. A distractor as set forth in claim 16 wherein the material has a transition temperature lower than an anticipated body temperature of the patient.

18. A distractor as set forth in claim 15 wherein the sheet having the spiral cross section has at least one complete turn in the expanded configuration.

* * * * *